(12) United States Patent
Willing

(10) Patent No.: US 10,444,193 B2
(45) Date of Patent: Oct. 15, 2019

(54) METHOD AND ARRANGEMENT FOR THE ANALYSIS OF GAS CHARACTERISTICS

(71) Applicant: RÜEGER S.A., Crissier (CH)

(72) Inventor: Bert Willing, Blonay (CH)

(73) Assignee: RÜEGER S.A., Crissier (CH)

( * ) Notice: Subject to any disclaimer, the term of this patent is extended or adjusted under 35 U.S.C. 154(b) by 231 days.

(21) Appl. No.: 15/643,926

(22) Filed: Jul. 7, 2017

(65) Prior Publication Data

US 2018/0011058 A1 Jan. 11, 2018

(30) Foreign Application Priority Data

Jul. 11, 2016 (EP) ..................................... 16178814

(51) Int. Cl.
 *G01N 29/024* (2006.01)
 *G01N 29/44* (2006.01)
 *G01N 33/00* (2006.01)
 *G01N 29/32* (2006.01)

(52) U.S. Cl.
 CPC ........... *G01N 29/024* (2013.01); *G01N 29/32* (2013.01); *G01N 29/4409* (2013.01); *G01N 33/0031* (2013.01); *G01N 2291/012* (2013.01); *G01N 2291/0215* (2013.01); *G01N 2291/02845* (2013.01); *G01N 2291/02881* (2013.01); *G01N 2291/103* (2013.01)

(58) Field of Classification Search
 CPC .. G01N 29/024; G01N 29/22; G01N 29/4409; G01N 33/0031; G01N 2291/012; G01N 2291/02845; G01N 2291/103
 USPC .................................. 73/24.06, 29.01, 31.05
 See application file for complete search history.

(56) References Cited

U.S. PATENT DOCUMENTS

| 5,152,174 A | 10/1992 | Labudde |
| 5,846,831 A * | 12/1998 | Silvis ................... G01N 1/2252 436/55 |
| 6,487,916 B1 * | 12/2002 | Gomm .................... G01F 1/667 73/861.27 |
| 2002/0124660 A1 * | 9/2002 | Drzewiecki ............... F15C 1/22 73/861.19 |

FOREIGN PATENT DOCUMENTS

| GB | 784 146 A | 10/1957 |
| WO | WO 02/071000 A1 | 9/2002 |
| WO | WO 2013/179202 A2 | 12/2013 |

OTHER PUBLICATIONS

Extended European Search Report dated Oct. 17, 2016 for corresponding European Application No. EP 16 17 8814.6.

* cited by examiner

*Primary Examiner* — Benjamin R Schmitt
(74) *Attorney, Agent, or Firm* — Renner, Otto, Boisselle & Sklar, LLP

(57) ABSTRACT

A sensor arrangement and method for measuring the speed of sound in a gas to determine gas characteristics, such as composition, temperature and/or humidity of the gas. The sensor arrangement includes a sound sender, first and second sound receivers, and a signal processing unit. The sound sender and sound receivers are arranged such that the travel distance of the sound provided by the sender to the first receiver is different from the travel distance of the sound provided by the sender to the second receiver. Further the arrangement includes the signal processing unit connected with the sender and the receivers which operates to determine the gas characteristics.

14 Claims, 1 Drawing Sheet

METHOD AND ARRANGEMENT FOR THE ANALYSIS OF GAS CHARACTERISTICS

CROSS REFERENCE TO RELATED APPLICATION

This application is based upon and claims the benefit of priority of European Patent Application No. 16 178 814.6, filed on Jul. 11, 2016, the entire content of which is incorporated herein by reference.

TECHNICAL FIELD

The present invention concerns a method for measuring the speed of the sound in a gas suitable for the determination of gas characteristics, especially the composition of the gas, the temperature and/or the humidity of the gas, and a speed of sound based gas sensor arrangement adapted to measure that gas characteristics comprising sound sending means and sound receiving means and signal processing means. The present invention further concerns a method for determining the humidity of the scavenge air of an internal combustion engine.

BACKGROUND ART

It is well known to use the speed of sound in a gas for measuring its temperature/humidity or its composition since the speed of sound is only influenced by its temperature and its composition. Measuring the speed of sound can therefore yield the temperature for a gas with known composition, or the composition of a gas at the known temperature. The measurement can be performed with ultrasonic sound or none-ultrasonic sound. Thus, the term "sound" includes both kinds of sound. If the temperature of the gas is known, it is also possible to determine the humidity. The speed of sound is usually measured by determining the propagation time, i.e. the time an acoustic signal to travel the distance between a sender and a receiver. This can be done by sending pulsed signals and measuring the delay for the signal to be detected at the receiver, or by sending a continuous signal and measuring the phase angle between the excitation of the sender and the signal of the receiver. The use of speed of sound measurements is especially appropriate in cases where other measurement principles cannot be used, for example for measurements of the humidity over a large temperature range, for example 30 to 300° C. and/or at specific humidity between 0 and 100%.

The sensitivity of speed of sound measurements based on the measurement of the phase angle between sender signal and receiver signal is a function of $L \cdot f$, with L the distance between sender and receiver, and f the operating frequency of the sender. In some cases the measurement range is such that the measured phase angle span exceeds $2 \cdot \pi$, so that the measurement result becomes ambiguous. In cases where a speed of sound measurement has be done across the diameter of a tube with very high temporal resolution (for example, to measure the temperature variations of a highly dynamic process), f is given by the required temporal resolution and cannot be decreased. L is given by either the diameter of the tube, or by the near field limit of the ultrasonic sender and cannot be decreased at will.

It is therefore an object of the invention to propose a method and an arrangement which is able to measure gas characteristics, especially the gas composition, the temperature and/or the humidity, which overcomes the above drawbacks and allows a measurement with high accuracy of a gas having large temperature variations.

This object is solved according to the method for measuring the speed of sound and speed of sound-based gas sensor arrangement described herein.

SUMMARY

According to the invention the method comprises providing a sound sender and a first sound receiver and a second sound receiver, such that the travel distance of the sound provided by the sender to the first receiver is different from the travel distance of the sound provided by the sender to the second receiver, sending the sound from the sender to both of the receivers, and determining gas characteristics, especially the composition of the gas, the temperature and/or the humidity of the gas, from the different signals provided by the first and the second receiver.

Accordingly, the speed of sound based gas sensor arrangement according to the invention adapted to measure gas characteristics, especially the gas composition, the temperature and/or the humidity of a gas, comprises a sound sender as sound sending means and at least a first sound receiver and a second sound receiver as sound receiving means, arranged such that the travel distance of the sound provided by the sender to the first receiver is different from the travel distance of the sound provided by the sender to the second receiver. Further the arrangement comprises the signal processing means connected with the sender and the receivers which operate the sender and determine gas characteristics, especially the composition of the gas, the temperature and/or the humidity of the gas, from the different signals provided by the at least first and the second receiver.

If neither L nor f can be reduced for practical reasons, a solution is to employ two receivers at different distances from the sender L1 and L2, and to measure the two phase angles of the receiver's signals $\Phi 1$ and $\Phi 2$. In the relevant equations relating the phase angle and the distance to the measurement result, the phase angle $\Phi$ is then replaced by the phase angle difference $\Delta\Phi = \Phi 2 - \Phi 1$, and the length L is replaced by the difference in length $\Delta L = L2 - L1$.

In such a case, the use of a second microphone makes it possible to adjust $\Delta L$ such that over the required measurement span, $\Delta\Phi$ will not exceed $2 \cdot \pi$ without limiting the temporal resolution or operating the sensor within the near field.

Preferably, according to the invention the second receiver is arranged near the first receiver in the same direction from the sender thereby providing in general only one measuring section of the sound excited by the sender. In general it is possible to use more than two receivers, for example a third receiver, if it is necessary and appropriate to collect more accurate or more detailed data.

The use of a second microphone yields another advantage in cases where the ultrasonic sender generates a phase shift between the driving signal and the sound emission by itself. If this sender-generated phase angle is constant, it can be compensated by a calibration. However, in most cases the sender is based on a piezoelectric ceramics and is operated at its resonance frequency for maximum sound pressure. This resonance will introduce a phase shift, and this phase shift will change with ambient temperature, as the sender's resonance is ruled by material properties which change with temperature.

According to another preferred embodiment of the invention, the phase angle difference of the signals of the first and the second receiver for determination of gas characteristics, especially gas composition, temperature and/or humidity, is determined. Measuring the phase angle at two receivers placed at different locations from the sender will have the sender's phase shift afflicting both receivers equally, and measuring $\Delta\Phi$ will therefore entirely suppress the sender's phase shift. The phase angles of the two receivers can be measured separately (i.e. by a lock-in amplifier attributed to each receiver) and the phase angle difference can be calculated by post-processing.

In an alternative embodiment of the invention, the voltage amplitude between the first and the second receiver for determination of gas characteristics, especially gas composition, temperature and/or humidity, is determined. The signals of the two receivers can then be measured differentially by a lock-in amplifier. In this case, the amplitude of the measured differential signal varies as a function of the phase angle difference between its minimum at zero and $2\cdot\pi$ phase angle difference, and a maximum value at a phase angle difference of $\pi$. If the amplitudes of the receiver signals are identical (i.e. both receivers have exactly the same sensitivity), the minimum of the differential signal is zero, and its maximum is twice the signal of one single receiver. The amplitude of the differential signal can therefore only cover a span of the phase angle difference of $\pi$.

If both receivers have the same sensitivity, the phase angle of the differential signal corresponds exactly to the phase angle difference over a span of $2\cdot\pi$. If the sensitivities of the two receivers are not equal, the linear relationship between the phase of the differential signal and the phase angle difference becomes distorted and the unambiguous range limited. For large differences in sensitivity, the phase of the differential signal shows a sinusoidal variation as a function of the phase angle difference, which again reduces the useful measurement range to a span of the phase angle difference of $\pi$.

Both amplitude and phase of the differential signal are dependent on the individual sensitivities of the receivers, and the amplitude of the differential signal is additionally dependent on the amplitude of the emitted sound. The measurement of the differential signal will therefore be influenced by a degradation of any of the transducers.

Additionally, according to another embodiment of the invention, the method comprises differentially measuring the signals of the receivers and calculating gas characteristics, especially the temperature and/or the humidity, from the amplitude and the phase angle of the differential signal.

According to another embodiment of the invention, the method comprises suppressing a phase shift of the phase of the sender signal due to the operation mode of the sender by common-mode rejection based on the signals of the first and second receiver.

In a further embodiment of the invention, the method comprises separately measuring the phase angles of the signals of the receivers and calculating the phase angle difference in a further step.

A special application of the method described above lies in the measurement of the humidity of the engine scavenge air. For the right stoichiometric fuel rate in an internal combustion engine, most notably large industrial and marine engines, as well as some trucks and heavy machinery, it is necessary to measure the humidity in the scavenge air. Due to the high temperature and pressure in that region between a turbocharger and the combustion chamber, state-of-the-art measurement devices for determining the humidity are influenced by the gas conditions. In view of this, according to the preferred embodiment, the method described before can be used for adjustment the relationship between intake air and fuel of an internal combustion engine by determining the humidity of the engine scavenge air.

The speed of sound based gas sensor arrangement adapted to measure gas, especially the gas composition, the temperature and/or the humidity of a gas, according to the invention is able to perform the method explained above. The arrangement further comprises signal processing means to perform the respective features of the method as mentioned above.

In the following, embodiments of the invention are described in detail in connection with the drawings. However, the invention is not limited to the examples described in connection with the drawings and includes all embodiments covered by the claims and the description alone or in connection with each other.

DETAILED DESCRIPTION

In the following the invention is explained in connection with the arrangement in a gas pipe for example for the detection of engineering scavenge air humidity. However, the method and the arrangement also can be used in other applications, especially in applications with extreme environmental conditions for the arrangement and in which a wide range of measurement values are required.

Figure 1:
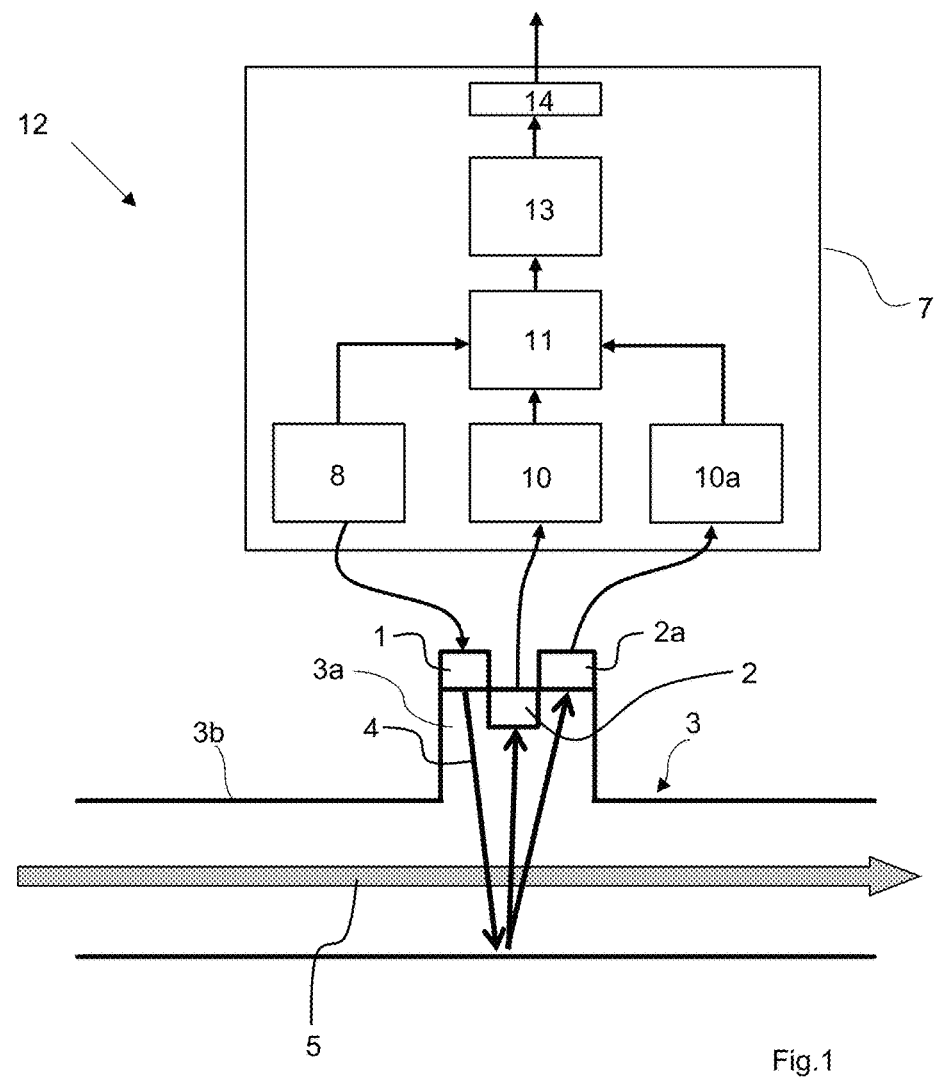
FIG. 1 a gas sensing arrangement in a gas pipe having a sender and two receivers on the same side of the gas pipe together with a block diagram of a signal processing unit comprising the signal processing means, and FIG. 2 another gas sensing arrangement in a gas pipe having sender and receivers on the opposite sides of the gas pipe.

FIG. 1 shows a gas sensing arrangement 12 comprising a sound sender 1 arranged in a recess 3a of a scavenge air gas pipe 3. In the recess 3a a first sound receiver 2 and a second sound receiver 2a are provided as well. As shown in the figure, the receivers 2, 2a are arranged close together but offset to each other. Due to the arrangement of sender 1 and receivers 2, 2a the propagation paths 4 between the sender 1 and the receivers 2, 2a of the sound emitted by the sender 1 extends through the same section of the volume of the pipe 3, i.e. the propagation paths 4 are close together.

However, the propagation paths 4 are of different length. Thus, sound emitted from sender 1 has to travel different distances to reach the receiver 2 or 2a. The propagation of the scavenge air is depicted with numeral 5.

The propagation paths 4 can also include a reflection of the sound at wall 3b of the gas pipe 3.

Sender 1 and the two receivers 2, 2a are connected to a signal processing unit 7 which comprises a sound function generator 8, which in this case is capable to provide ultrasound and is connected with the sender 1. The signal processing unit 7 further comprises a first pre-amplifier/AD converter 10 connected with the first receiver 2 and a second pre-amplifier/AD converter 10a connected with the second receiver 2a. The sound function generator 8 and the two pre-amplifier/AD converters 10, 10a are all connected with a lock-in amplifier 11 which is connected with a microprocessor 13, which controls the function of the total sensor arrangement. The lock-in amplifier 11 provides a signal indicating the phase angle between the signals provided by the first receiver 2 and the second receiver 2a. Number 14 indicates the output of the result for further processing the measured characteristic of the gas. In another advantageous embodiment, the lock-in amplifier 11 can be integrated digitally within the microprocessor 13. It is clear, that the lock-in amplifier 11 has two separate input channels and output channels and input for the reference signal in view of the independent measurement of the phases.

Figure 2:
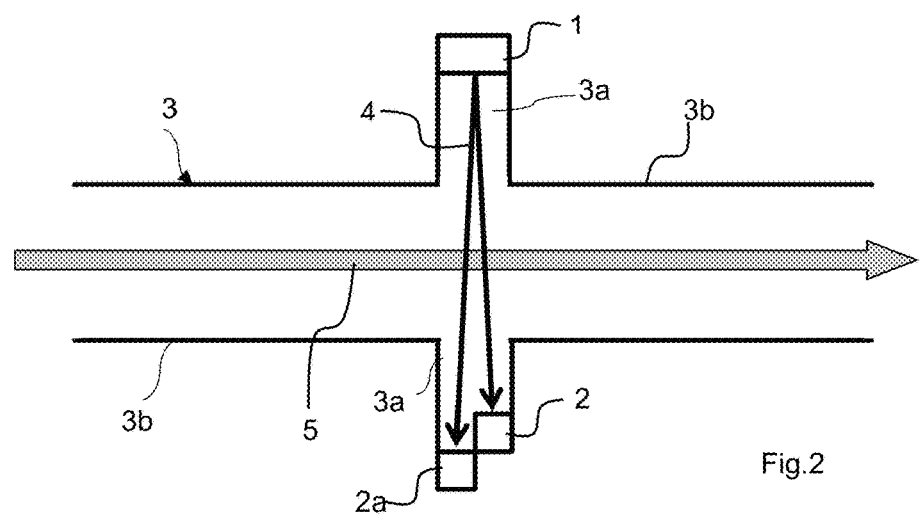

FIG. 2 shows another arrangement of the sender 1 and the first receiver 2 and the second receiver 2a, which are both arranged opposite to the sender 1 on the other side of the gas pipe 3. The sender 1 as well as the receivers 2, 2a are arranged in different recesses 3a. In this embodiment the receivers 2, 2a are arranged such that the distance between the sender 1 and the two receivers 2, 2a is different. The sender 1 and the receivers 2, 2a are connected to the signal processing unit 7 in the same way as shown in FIG. 1.

The invention claimed is:

1. A method for measuring the speed of sound in a gas flow to determine gas characteristics, comprising providing a sound sender and a first sound receiver and a second sound receiver, such that the travel distance of the sound provided by the sender to the first receiver is different from the travel distance of the sound provided by the sender to the second receiver,
   arranging the second receiver close together to the first receiver such that the receivers thereby provide only one measuring section of the sound excited by the sender,
   offsetting the receivers in a direction perpendicular to the gas flow to create the travel distance difference,
   sending the sound from the sender to both of the receivers such that the sound travels across the gas flow,
   determining gas characteristics from the different signals provided by the first and the second receiver.

2. The method according to claim 1, comprising determining the phase angle difference of the signals of the first and the second receiver for determination of gas characteristics.

3. The method according to claim 1, comprising differentially measuring the voltage amplitude between the first and the second receiver for determination of gas characteristics.

4. The method according to claim 2, comprising suppressing a phase shift of the phase of the sender signal due to the operation mode of the sender by common-mode rejection based on the signals of the first and second receiver.

5. The method according to claim 1, comprising separately measuring the phase angles of the signals of the receivers and calculating the phase angle difference in a further step.

6. A method comprising determining humidity of an engine scavenge air using the method of claim 1.

7. The method according to claim 1, wherein the measured gas characteristics is at least one of gas composition, humidity and temperature.

8. A speed of sound based gas sensor arrangement adapted to measure gas characteristics in a gas flow, comprising a sound sender and a sound receiver connected to a signal processor, wherein the sound receiver comprises at least a first sound receiver and a second sound receiver, the sound sender and the sound receivers arranged such that the sound provided by the sound sender to the sound receivers travels across the gas flow and the travel distance of the sound provided by the sound sender to the first sound receiver is different from the travel distance of the sound provided by the sound sender to the second sound receiver, wherein the second sound receiver is arranged close to the first sound receiver such that the sound receivers thereby provide only one measuring section of the sound excited by the sound sender, wherein the second sound receiver is arranged offset to the first sound receiver in a direction perpendicular to the gas flow to create a travel distance difference, and wherein the signal processor operates the sender and determines gas characteristics from the different signals provided by the at least first and the second sound receiver.

9. The arrangement according to claim 8, wherein the signal processor determines the phase angle difference of the signals of the first and the second receiver for determination of gas characteristics.

10. The arrangement according to claim 8, wherein the signal processor measures the voltage amplitude between the first and the second receiver for determination of gas characteristics.

11. The arrangement according to claim 9, wherein the signal processor suppresses a phase shift of the phase of the sender signal due to the operation mode of the sender by common-mode rejection based on the signals of the first and second receiver.

12. The arrangement according to claim 8, wherein the signal processor separately measures the phase angles of the signals of the receivers and calculates the phase angle difference in a further step.

13. The arrangement according to claim 8, wherein the signal processor differentially measures the signals of the receivers and calculates gas characteristics.

14. The arrangement according to claim 8, wherein the measured gas characteristics is at least one of gas composition, humidity and temperature.

* * * * *